United States Patent
Goldstein

(10) Patent No.: US 8,399,609 B2
(45) Date of Patent: Mar. 19, 2013

(54) TREATING OR PREVENTING EXTRACELLULAR MATRIX BUILD-UP

(75) Inventor: Allan L. Goldstein, Washington, DC (US)

(73) Assignee: RegeneRx Biopharmaceuticals, Inc., Rockville, MD (US)

(*) Notice: Subject to any disclaimer, the term of this patent is extended or adjusted under 35 U.S.C. 154(b) by 959 days.

(21) Appl. No.: 10/591,527

(22) PCT Filed: Mar. 7, 2005

(86) PCT No.: PCT/US2005/007448
§ 371 (c)(1), (2), (4) Date: Jun. 28, 2007

(87) PCT Pub. No.: WO2005/087805
PCT Pub. Date: Sep. 22, 2005

(65) Prior Publication Data
US 2010/0226911 A1   Sep. 9, 2010

Related U.S. Application Data

(60) Provisional application No. 60/549,911, filed on Mar. 5, 2004.

(51) Int. Cl.
*A61K 39/395* (2006.01)
(52) U.S. Cl. ...... 530/300; 424/130.1; 514/56; 623/1.11; 623/1.42
(58) Field of Classification Search .......... None
See application file for complete search history.

(56) References Cited

U.S. PATENT DOCUMENTS

| 5,578,570 A | 11/1996 | Goldstein et al. |
| 2004/0117008 A1 | 6/2004 | Wnendt et al. |

FOREIGN PATENT DOCUMENTS

| WO | WO 99/49883 | * 10/1999 |
| WO | 00/06190 A1 | 2/2000 |
| WO | 0054806 A1 | 9/2000 |
| WO | 02/36143 A1 | 5/2002 |
| WO | 02065947 A2 | 8/2002 |
| WO | 03/020215 A2 | 3/2003 |
| WO | WO 03/020215 | * 3/2003 |
| WO | 03034938 A2 | 5/2003 |

OTHER PUBLICATIONS

Philp, D. et al., "Thymosin beta 4 and a synthetic peptide containing its actin-binding domain promote dermal wound repair in db/db diabetic mice and in aged mice", Would Repair and Regeneration, Jan. 2003, 11(1):19-24, XP-002441696.

Grant, D.S. et al. "Matrigel induces thymosin beta 4 gene in differentiating endothelial cells", Journal of Cell Science, (1995), 108(12):3685-3694, XP-002441697.

* cited by examiner

*Primary Examiner* — Christopher R. Tate
*Assistant Examiner* — Roy Teller
(74) *Attorney, Agent, or Firm* — Rothwell, Figg, Ernst & Manbeck, P.C.

(57) ABSTRACT

A method of treatment for treating, preventing, inhibiting or reducing extracellular matrix build-up in a body tissue or a bodily fluid transport vessel, in a subject, includes administering to a subject in need of such treatment an effective amount of a composition including a peptide agent including amino acid sequence LKKTET, a conservative variant thereof, or a peptide agent that stimulates production of an LKKTET peptide, or a conservative variant thereof, in the tissue.

14 Claims, No Drawings

TREATING OR PREVENTING EXTRACELLULAR MATRIX BUILD-UP

CROSS-REFERENCE TO RELATED APPLICATIONS

The present application claims benefit of U.S. Provisional Application No. 60/549,911, filed Mar. 5, 2004.

BACKGROUND OF THE INVENTION

1. Field of the Invention

The present invention relates to the field of treating or preventing extracellular matrix build-up in a body tissue or a bodily fluid transport vessel.

2. Description of the Background Art

Plaque and extracellular matrix build-up in body tissue and vessels, including myocardial and coronary vessels, can be a serious, life-threatening problem. Such build-up may be due to, but is not limited to, tissue damage, clotting abnormalities, vessel occlusion, defects or abnormalities and other causes and events. There are a number of compounds, devices and procedures which, when given within prescribed time frames, may serve to reduce or eliminate such plaque or occlusions, however, often only temporarily. These include angioplasty and mechanical devices such as stents, as well as pharmaceuticals and dietary modifications. Unfortunately, in many cases, the occlusive build-up of plaque and extracellular matrix molecules continues (restenosis) even after such procedures.

There remains a need in the art for methods of treatment for treating, preventing, inhibiting or reducing extracellular matrix build-up in a body tissue or a bodily fluid transport vessel.

SUMMARY OF THE INVENTION

In accordance with one aspect, a method of treatment for treating, preventing, inhibiting or reducing extracellular matrix build-up in a body tissue or a bodily fluid transport vessel, in a subject, comprises administering to a subject in need of such treatment an effective amount of a composition comprising a peptide agent comprising amino acid sequence LKKTET, a conservative variant thereof, or a stimulating agent that stimulates production of an LKKTET peptide, or a conservative variant thereof, in said tissue, so as to inhibit extracellular matrix build-up in a body tissue or a bodily fluid transport vessel.

DETAILED DESCRIPTION OF THE INVENTION

Without being found to any specific theory, actin-sequestering peptides such as thymosin beta 4 (T$\beta$ 4, T$\beta_4$ or TB4) and other agents including actin-sequestering peptides or peptide fragments containing amino acid sequence LKKTET or conservative variants thereof, promote reversal or prevention of extracellular matrix build-up in a body tissue or a bodily fluid transport vessel.

Thymosin beta 4 was initially identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

The present invention may also be utilized to treat, prevent, inhibit or reduce extracellular matrix build-up (e.g., plaque build-up) on or in a body tissue such as brain or neural tissue.

It has been shown that T$\beta$4 can induce angiogenesis and reduce inflammation in several rodent models. T$\beta$4 also sequesters and regulates polymerization of actin and may stimulate collegen synthesis and other extracellular matrix molecules following wounding. However, there has been no known indication that such properties may be useful in treating extracellular matrix build-up in a body tissue or a bodily fluid transport vessel such as occlusions and restenosis of coronary vessels and surrounding tissue such as heart valves and septa. The ability to induce angiogenesis, decrease inflammation, and depolymerize actin is useful in treating restenosis and similar indications in humans.

T$\beta$4 and other actin sequestering peptides that contain the actin binding motif and amino acid sequence LKKTET regulate chemotactic endothelial cells and can accelerate wound healing and modulate a number of key inflammatory cytokines e.g., IL-1 B$\alpha$, IL-18 and chemokines such as MIP1-$\alpha_1$ MIP-1$\beta$ and MIP2.

As endothelial cells differentiate into capillaries or following any tissue injury, the gene for T$\beta$4 is turned on and the levels of T$\beta$4 mRNA and T$\beta$4 are elevated within the cells and surrounding tissues. T$\beta$4 accelerates healing and can be covalently linked to fibrin and other extracellular molecules such as collagen. T$\beta$4 and T$\beta$4 analogues and other actin-sequestering molecules containing the amino acid motif LKKTET, when covalently coupled to stents and/or administered prior to, during and/or after angioplasty can prevent or reverse restenosis and stenosis. T$\beta$4 and other peptides containing the LKKTET motif also act as chemotactic and angiogenic factors for endothelial cells and thus can prevent or reduce the build up of plaque in coronary vessels and surrounding tissues.

A significant problem in chronic wounds and when utilizing stents is the production of an over-abundance of inflammatory cytokines in the injured tissue. The ability of T$\beta$4 to down regulate a number of key cytokines and chemokines and to accelerate the process of wound healing in normal and immunosuppressed animals can inhibit restenosis where inflammation, inflammatory intermediates and white cell infiltration have been implicated. With respect to injuries to the eye, it has been demonstrated a that T$\beta$4 results in significant reduction in polymorponuclear leukocyte (PMN) infiltiation and clear reduction in a number of inflammatory cytokines.

The invention provides a method for the prevention, healing, or reduction of build-up of plaque in coronary vessels and surrounding tissues, heart valves and heart septa due to physiological insults, inflammation, cholesterol, or other factors which may occur in a subject in need of such treatment following stenting or angioplasty by the application of a therapeutically effective amount of a peptide agent or stimulating agent as described herein.

The invention includes covalently or otherwise linking a peptide agent or stimulating agent as described herein to stents or other medical devices or molecules used to prevent stenosis or restenosis.

The invention includes covalently or otherwise linking a peptide agent or stimulating agent as described herein to a physiologically acceptable adhesive such as fibrin-glue or similar compounds following coronary bypass surgery to prevent stenosis or restinosis.

The invention includes applying a therapeutically effective amount of a peptide agent or stimulating agent as described herein to a site on a periodic basis during a course of therapy to prevent or reduce stenosis or restenosis.

The invention includes administering a peptide agent or stimulating agent as described herein prior to, during and/or following angioplasty to prevent stenosis or restenosis.

Devices and procedures which may be utilized to affect an increase in blood flow through a blood vessel include, but are not limited to, arterial stents, venous stents, cardiac catherizations, carotid stents, aortic stents, pulmonary stents, angioplasty, heart and/or other bypass surgery and/or neurosurgery. The LKKTET peptide can be administered before, during and/or after utilization of one or more of such devices and/or procedures.

In accordance with one embodiment, the invention is a method of treatment for treating, preventing, inhibiting or reducing extracellular matrix build-up in a body tissue or a bodily fluid transport vessel, in a subject, comprising administering to a subject in need of such treatment an effective amount of a composition comprising a peptide agent, which may be a polypeptide comprising amino acid sequence LKK-TET, or a conservative variant thereof having extracellular matrix build-up-inhibiting activity, preferably Thymosin β 4, and/or Tβ4 isoforms, analogues or derivatives, including KLKKTET, LKKTETQ, oxidized Tβ4, Tβ4 sulfoxide, N-terminal variants of Tβ4, C-terminal variants of Tβ4, and agonists or antagonists of Tβ4.

Compositions which may be used in accordance with the present invention include peptide agents such as Thymosin β4 (T β4), and/or, or a peptide agent other than Tβ4, such as Tβ4 isoforms, analogues or derivatives, including oxidized Tβ4, Tβ4 sulfoxide, N-terminal variants of Tβ4, C-terminal variants of Tβ4 and antagonists of Tβ4, polypeptides or peptide fragments comprising or consisting essentially of the amino acid sequence LKKTET or conservative variants thereof, having extracellular matrix build-up-inhibiting activity. International Application Serial No. PCT/US99/17282, incorporated herein by reference, discloses isoforms of Tβ 4 which may be useful in accordance with the present invention as well as amino acid sequence LKKTET and conservative variants thereof, which may be utilized with the present invention. International Application Serial No. PCT/GB99/00833 (WO 99/49883), incorporated herein by reference, discloses oxidized Thymosin β 4 which may be utilized in accordance with the present invention. Although the present invention is described primarily hereinafter with respect to T β4 and T β4 isoforms, it is to be understood that the following description is intended to be equally applicable to amino acid sequence LKKTET, peptides and fragments comprising or consisting essentially of LKKTET, conservative variants thereof having extracellular matrix build-up-inhibiting activity, and/or Tβ4 isoforms, analogues or derivatives, including oxidized Tβ4, Tβ4 sulfoxide, N-terminal variants of Tβ4, C-terminal variants of Tβ4 and antagonists of Tβ4.

In one embodiment, the invention provides a method of treatment for treating, preventing, inhibiting or reducing extracellular matrix build-up in a body tissue or a bodily fluid transport vessel, in a subject, by contacting the tissue with an effective amount of a composition which contains a peptide agent as described herein. As non-limiting examples, the tissue may be selected from heart tissue such as heart valves and/or heart septa, and blood vessels such as myocardial and coronary vessels, of a subject. The contacting may be directly or systemically. Examples of direct administration include, for example, contacting the tissue, or a stent or other device to be contacted with the tissue, with a matrix, adhesive, solution, lotion, salve, gel, cream, paste, spray, suspension, dispersion, hydrogel, ointment, or oil comprising a peptide agent as described herein. Systemic administration includes, for example, inhalation, and/or intravenous, intraperitoneal, and/or intramuscular injections of a composition containing a peptide agent as described herein, in a pharmaceutically acceptable carrier such as water for injection.

Peptide agents for use in the invention, as described herein, may be administered in any effective amount. For example, a peptide agent as described herein may be administered in dosages within the range of about 0.0001-1,000,000 micrograms, preferably in amounts within the range of about 0.01-5,000 micrograms, more preferably about 0.1-50 micrograms, and most preferably within the range of about 1-30 micrograms.

In accordance with one particularly preferred embodiment, a peptide agent as described herein is administered at a dosage within a range of about 0.1 microgram to about 10 mg/kg body weight (BW) of said subject. In accordance with one embodiment, a peptide agent as described herein is administered intravenously at a dosage of about 1-10 mg/kg body weight of said subject.

A composition in accordance with the present invention can be administered as a single administration, daily, every other day, every other week, every other month, etc., with a single application or multiple applications per day of administration, such as applications 2, 3, 4 or more times per day of administration.

Many Tβ 4 isoforms have been identified and have about 70%, or about 75%, or about 80% or more homology to the known amino acid sequence of Tβ 4. Such isoforms include, for example, Tβ4$^{ala}$, Tβ 9, T β10, Tβ 11, T β12, T β13, T β14 and Tβ 15. Similar to T β4, the Tβ 10 and Tβ 15 isoforms have been shown to sequester actin. Tβ 4, T β10 and Tβ 15, as well as these other isoforms share an amino acid sequence, LKK-TET, that appears to be involved in mediating actin sequestration or binding. T β4 can modulate actin polymerization (e.g. β-thymosins appear to depolymerize F-actin by sequestering free G-actin). Tβ 4's ability to modulate actin polymerization may be due to its ability to bind to or sequester actin via the LKKTET sequence. Thus, as with Tβ 4, other proteins which are anti-inflammatory and/or bind or sequester actin, or modulate actin polymerization, including Tβ 4 isoforms having the amino acid sequence LKKTET, may be effective, alone or in a combination with T β4, as set forth herein.

Peptide agents as described herein, such as Tβ4, can impact tissue by upregulating metabolic and signaling enzymes such as the phosphatidylinositol 3-kinase (P13-K)/Akt (protein kinase β) pathway. Upregulating P13-K)/Akt and downstream phosphorylated Bad and proline rich Akt survival kinase protects certain cells. In addition peptide agents as described herein, such as Tβ4 and Tβ4 isoforms or oxidized forms of Tβ4 by virtue of their ability to downregulate inflammatory cytokines such as IL-18 and chemokines such as IL-8 and enzymes such as caspace 2, 3, 8 and 9 protects certain cells. Peptide agents as described herein, such as Tβ4 decrease inflammatory chemokine, cytokine and capase activity.

Thus, it is specifically contemplated that known Tβ 4 isoforms, such as T β4$^{ala}$, Tβ 9, T β10, T β11, T β12, T β13, T β14 and T β15, as well as Tβ 4 isoforms not yet identified, will be useful in the methods of the invention. As such, T β4 isoforms are useful in the methods of the invention, including the methods practiced in a human subject. The invention therefore further provides pharmaceutical compositions comprising Tβ 4, as well as Tβ 4 isoforms Tβ 4$^{ala}$, Tβ 9, Tβ 10, Tβ 11, Tβ 12, T β13, Tβ 14 and Tβ 15, and a pharmaceutically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET, for example, can similarly be employed in the methods of the invention. Such proteins may include gelsolin, vitamin D binding protein (DBP), profilin, cofilin, depactin, Dnase1, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, Dnase1, vilin, fragmin, severin, capping protein, β-actinin and acumentin as set forth herein. Thus, the invention includes the use of an polypeptide comprising the amino acid sequence LKKTET and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

T β4 has been localized to a number of tissue and cell types and thus, agents which stimulate the production of an LKKTET peptide such as Tβ 4 or another peptide agent as described herein, can be added to or comprise a composition to effect production a peptide agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α"1 (Tα"1) and vascular endothelial growth factor (VEGF). More preferably, the stimulating agent is transforming growth factor beta (TGF-β) or other members of the TGF-β superfamily.

In accordance with one embodiment, subjects are treated with a stimulating agent that stimulates production in the subject of a peptide agent as defined herein.

Additionally, other agents that assist in reduction of extracellular matrix build-up in a body tissue or a bodily fluid transport vessel may be administered with or added to a composition along with a peptide agent as described herein. For example, and not by way of limitation, a peptide agent as described herein alone or in combination can be administered with or added in combination with any one or more of the following agents: plaque-reducing agents such as chelating agents (e.g., EDTA) and cholesterol reducing agents, antioxidants, antibiotics, VEGF, KGF, FGF, PDGF, TGFβ, IGF-1, IGF-2, IL-1, prothymosin α" and/or thymosin α"1 in an effective amount. Preferably such other agents are administered at dosages with the range of 0.0001-1,000,000 micrograms.

The invention also includes a pharmaceutical composition comprising a therapeutically effective amount of a peptide agent as described herein in a pharmaceutically acceptable carrier. Such carriers include those listed herein.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include a peptide agent as described herein at a concentration within the range of about 0.001-50% by weight, more preferably within the range of about 0.01-0.1% by weight, most preferably about 0.05% by weight.

The therapeutic approaches described herein involve various routes of administration or delivery of a peptide agent as described herein, including any conventional administration techniques (for example, but not limited to, direct administration, local injection, inhalation, systemic administration, etc.), to a subject. The methods and compositions using or containing a peptide agent as described herein may be formulated into pharmaceutical compositions by admixture with pharmaceutically acceptable non-toxic excipients or carriers.

The invention includes use of antibodies which interact with, enhance or inhibit a peptide agent as described herein. Antibodies which consist essentially of pooled monoclonal antibodies with different epitopic specificities, as well as distinct monoclonal antibody preparations are provided. Monoclonal antibodies are made from antigen containing fragments of the protein by methods well known to those skilled in the art as disclosed in PCT/US99/17282, supra. The term antibody as used in this invention is meant to include monoclonal and polyclonal antibodies.

In yet another embodiment, the invention provides a method of treating a subject by administering an effective amount of stimulating agent which modulates gene expression. The term "modulate" refers to inhibition or suppression of expression when a peptide agent as described herein is over expressed, and induction of expression when a peptide agent as described herein is underexpressed. The term "effective amount" means that amount of stimulating agent which is effective in modulating gene expression of a peptide agent as described herein, resulting in reducing extracellular matrix build-up in a body tissue or a bodily fluid transport vessel. A stimulating agent which modulates gene expression of a peptide agent as described herein may be a polynucleotide, for example. The polynucleotide may be an antisense, a triplex agent, or a ribozyme. For example, an antisense directed to the structural gene region or to the promoter region of a peptide agent as described herein may be utilized. The stimulating agent which modulates gene expression of a peptide agent as described herein may also be a small interfering RNAs (siRNAs).

In another embodiment, the invention provides a method for utilizing compounds that modulate activity of a peptide agent as described herein. Compounds that affect activity of a peptide agent as described herein (e.g., antagonists and agonists) include peptides, peptidomimetics, polypeptides, chemical compounds, minerals such as zincs, and biological agents.

A method for screening for a stimulating agent as defined herein, comprises contacting a tissue exhibiting extracellular matrix build-up in a body tissue or a bodily fluid transport vessel with a candidate compound; and measuring activity in said tissue of an LKKTET peptide, wherein an increase of activity of said peptide in said tissue, compared to a level of activity of said peptide in a corresponding tissue lacking said candidate compound, indicates that said compound is capable of inducing said stimulating agent.

A method for screening for a peptide agent as defined herein, comprises contacting a tissue exhibiting extracellular matrix build-up in a body tissue or a bodily fluid transport vessel, with a candidate compound; and measuring reduction in said tissue of said extracellular matrix build-up, wherein a reduction of said extracellular matrix build-up in said tissue, compared to extracellular matrix build-up in a corresponding tissue lacking said candidate compound, indicates that said compound is capable of treating, preventing, inhibiting or reducing extracellular matrix build-up in a body tissue or a bodily fluid transport vessel.

EXAMPLE 1

0.1 ug to 1 ug per kg body weight of thymosin B4 (TB4) is administered by cardiac catheterization immediately following angioplasty and the patient then receives 600 ug to 6 mg TB4 intravenously per kg body weight (BW) two to four times per day for a period up to seven days. The amount and duration of treatment is dependent on the extent of ventricular damage following an acute myocardial infarction as measured by electrocardiography and nuclear imaging at the time of angiography and during the initial hospitalization of the patient.

EXAMPLE 2

0.1 ug to 1 ug per kg/BW of TB4 is administered by cardiac catherization immediately after angioplasty and/or stenting. The patient then receives by IV administration 600 ug to 6 mg/kg BW two to four times/day for a period of up to seven days following an MI. Preservation of heart muscle and reduction in restenosis is measured by electrocardiography and monitored by nuclear imaging or other diagnostic methods.

EXAMPLE 3

TB4 is administered IV at a dosage of 1 mg to 10 mg/kg BW/daily for up to 30 days to reduce coronary blockage due to plaque formation.

EXAMPLE 4

Thymosin Fractin 5 (TF5) inhibits ADP-induced platelet aggregation in a dose dependent manner. Platelet aggregation is inhibited by thymic epithelial cell culture supernatants and by TF5. Thymosins preparations containing thymosin beta 4 (Tβ4) affect the level of intracellular cAMP and cGMP in human and murine lymphocyctes. Evaluation of platelet cGMP by agents such as carbachol and endothelium derived relaxing factor leads to impaired platelet aggregation. On the other hand, platelets contain and release active substances which act as mediators of tissue ingury in immunological diseases. The correlation between the degree of platelet aggregation and intracellular levels of cAMP has been studied extensively. At present there is little doubt that inhibitory effect of various agents on platelet aggregation is caused by the accumulation of intracellular cAMP.

Platelet adherence to the endothelial surface of coronary artery plaques is thought to be rapidly followed by accumulation of activated platelets, an inflammatory cascade of chemokins and cytokines and PMN infiltration. Several studies over the past decade have implicated platelet-activating factor (PAF) in cardiovascular disease. PAF initiates a series of molecular events at the level of the endothelial cells of the coronaries which alter vascular permeability, induces hyperlipemia, inflammation, and PMN activation, leading to coronary thrombus formation and providing the clinical pathophysiologic seen in unstable angina, plaque formation, and myocardial infarction. In addition, the adherence of platelets to the extra cellular matrix of endothelial cells can initiate an inflammatory cascade leading to plaque formation and restinosis. Platelet-activating factor (PAF) is a significant player in accelerating platelet aggregation, plaque formation, and in arteriosclerosis.

Platelet Aggregation Assay

The inhibitory effects of Tβ4 on platelet aggregation were tested using a Payton duo-channel aggregometer. This aggregometer produces a plot of % light transmission (directly proportional to % aggregation) vs. time.

For each experiment, one 9 ml blood sample was drawn from a fasting, non-smoking, healthy subject into a propylene tube containing 1 ml of 3.8% sodium-citrate (anti-coagulant). This blood sample was then diluted with 2 ml of phosphate buffer (phosphate-buffer saline with 11 mM glucose and 3 mM sodium citrate). Dilution with phosphate buffer aids in stabilization of the platelet environment and retention of platelet activity for a longer period of time. Platelet-rich plasma (PRP) was prepared by centrifuging the blood for 3 min at 2300 RPM. After removal of PRP, the volume of the remaining blood was brought up to 10 ml by adding phosphate buffer, and the sample was once again centrifuged for the preparation of platelet-poor (PPP). To obtain PPP, we centrifuged the blood for 10 min at 2800 RPM.

Platelet aggregation tests were performed by recording % light transmission (vs. time) through samples of PRP. Before each assay, the aggregometer was adjusted such that PRP gave no light transmission. For aggregation assays, duplicate samples (0.4 ml) of PRP were incubated with 1 mM $CaCl_2$ (to restore the physiologic concentration of $Ca^{++}$) for 1 min at 37° C. Different amounts of Tβ4, ranging for 20 to 300 ng, dissolved in 30 μl of distilled/deionized water, were added to each assay. The mixture was then incubated and stirred for an additional 2 min before aggregation was induced with an agonist.

Among the agonists used in the experiments were ADP, epinephrine, arachidonic acid, thrombin, collagen (Sigma Chemicals), and PAF (Platelet-activating factor)-16 (from Calbiochem). Concentrations of these reagents were 1 μm, 10 μm, 100 μg/ml, 0.2 NIH units, 0.05 mg/ml, and 20 ng/ml respectively. Two control assays were run at the beginning and end of each experiment. An assay without Tβ4 (but with an equivalent volume of $H_2O$) constitutes a control, and the % light transmission produced by each control is assigned a value of % 100 for each experiment. For the measurement of % inhibition caused by Tβ4, light transmission in a Tβ4 assay was compared to the average light transmission in the start and end controls, using the following formula:

$$\% \text{ Overall inhibition} = \frac{\text{Control} - T\beta4\text{-assay}}{\text{Control}} \times 100$$

The results are shown in table 1.

TABLE 1

Inhibitory Effect of Tβ4 on PAF-16-induced Aggregation of Human Blood Platelets

| Amount Tβ4 | # Of Assays | Average % Inhibition of Aggregation |
|---|---|---|
| — | 4 | 0 |
| 20 ng | 4 | 50 |
| 40 ng | 3 | 90 |
| 60 ng | 4 | 100 |
| 80 ng | 4 | 95 |
| 100 ng | 4 | 92 |
| 300 ng | 4 | 84 |

As shown in table 1, Tβ4, by virtue of its ability to significantly inhibit human platelet aggregation, provides an avenue for the prevention and/or reduction in the progression of plaque formation and restenosis.

The invention claimed is:

1. In a subject with extracellular matrix build-up in a body tissue or a bodily fluid transport vessel, a method of treating or reducing said extracellular matrix build-up in a body tissue or a bodily fluid transport vessel comprising administering a composition comprising a peptide agent selected from the group consisting of Thymosin β4 (Tβ4) and oxidized Tβ4 in an amount effective so as to inhibit said extracellular matrix build-up in a body tissue or a bodily fluid transport vessel of said subject.

2. The method of claim 1 wherein said peptide agent comprises Tβ4.

3. The method of claim 1 wherein said peptide agent is administered to said subject at a dosage within a range of about 1-10 mg/kg body weight of said subject.

4. The method of claim 1 wherein said agent is administered by direct administration to said tissue, or by intravenous, intraperitoneal, intramuscular, subcutaneous, inhalation, transdermal or oral administration, to said subject.

5. The method of claim 1 wherein said composition is administered systemically.

6. The method of claim 1 wherein said composition is administered directly.

7. The method of claim 1 wherein said composition is comprised of a matrix, adhesive, solution, gel, crème, paste, lotion, spray, suspension, dispersion, salve, hydrogel or ointment formulation.

8. The method of claim 1 wherein said peptide agent is a recombinant or synthetic peptide.

9. The method of claim 1 wherein said Tβ4 is administered in conjunction with utilization in said subject of at least one of an arterial stent, venous stent, cardiac catheterization, corroded stent, aortic stent, pulmonary stent, angioplasty, bypass surgery or neurosurgery.

10. The method of claim 1 wherein said matrix build-up comprises plaque present in at least one of a coronary vessel, heart valve or heart septa of said subject.

11. The method of claim 1 wherein said Tβ4 is linked to a physiologically acceptable adhesive.

12. The method claim 1 wherein said Tβ4 is administered to said subject so as to treat, prevent, inhibit or reduce stenosis or restenosis in said subject.

13. The method of claim 12 wherein said Tβ4 is administered at least one of prior to, during or following angioplasty in said subject.

14. The method of claim 1 wherein said Tβ4 is administered, in combination with at least one plaque-reducing agent or cholesterol-reducing agent.

* * * * *

UNITED STATES PATENT AND TRADEMARK OFFICE
CERTIFICATE OF CORRECTION

PATENT NO.       : 8,399,609 B2                                            Page 1 of 1
APPLICATION NO. : 10/591527
DATED            : March 19, 2013
INVENTOR(S)      : Allan L. Goldstein It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1402 days.

Signed and Sealed this

First Day of September, 2015

Michelle K. Lee
*Director of the United States Patent and Trademark Office*